US012611376B2

(12) United States Patent
Ellis

(10) Patent No.: US 12,611,376 B2
(45) Date of Patent: **\*Apr. 28, 2026**

(54) DRUG DELIVERING STRETCH RING

(71) Applicant: JelliSee Ophthalmics Inc., McLean, VA (US)

(72) Inventor: Forrest J. Ellis, McLean, VA (US)

(73) Assignee: JELLISEE OPHTHALMICS INC., McLean, VA (US)

( \* ) Notice: Subject to any disclaimer, the term of this patent is extended or adjusted under 35 U.S.C. 154(b) by 318 days.

This patent is subject to a terminal disclaimer.

(21) Appl. No.: 18/384,679

(22) Filed: Oct. 27, 2023

(65) Prior Publication Data

US 2024/0139099 A1 May 2, 2024

Related U.S. Application Data

(60) Provisional application No. 63/419,738, filed on Oct. 27, 2022.

(51) Int. Cl.
| | |
|---|---|
| *A61K 9/00* | (2006.01) |
| *A61F 2/16* | (2006.01) |
| *A61K 31/56* | (2006.01) |
| *A61K 31/728* | (2006.01) |
| *A61K 47/56* | (2017.01) |

(52) U.S. Cl.
CPC .............. *A61K 9/0051* (2013.01); *A61F 2/16* (2013.01); *A61K 31/56* (2013.01); *A61K 31/728* (2013.01); *A61K 47/56* (2017.08); *A61F 2210/0004* (2013.01); *A61F 2210/0057*

(2013.01); *A61F 2230/0006* (2013.01); *A61K 2121/00* (2013.01); *A61K 2300/00* (2013.01)

(58) Field of Classification Search
CPC ..................................................... A61K 9/0051
See application file for complete search history.

(56) References Cited

U.S. PATENT DOCUMENTS

| | | | |
|---|---|---|---|
| 6,136,026 A | 10/2000 | Israel | |
| 2020/0405538 A1* | 12/2020 | Mandell | ............... A61K 31/519 |

FOREIGN PATENT DOCUMENTS

| | | |
|---|---|---|
| WO | 2008113043 A1 | 9/2008 |
| WO | 2022016130 A1 | 1/2022 |

OTHER PUBLICATIONS

Corresponding International Patent Application No. PCT/US2023/036125, International Search Report, date mailed Feb. 1, 2024.
(Continued)

*Primary Examiner* — Carlos A Azpuru
(74) *Attorney, Agent, or Firm* — Tarolli, Sundheim, Covell & Tummino LLP

(57) ABSTRACT

A polymer ring configured to fit around or adjacent to an intraocular lens is described. The polymer ring comprises a hyaluronic acid derivative and a drug. An intraocular lens comprising a polymer ring positioned on or adjacent to the intraocular lens is also described. In addition, a method of delivering a drug to an eye of a subject is described. The method includes inserting an intraocular lens into the eye of the subject, and positioning polymer ring onto at least a portion of the intraocular lens, wherein the polymer ring comprises a hyaluronic acid derivative and a drug.

8 Claims, 3 Drawing Sheets

B

(56)                    References Cited

OTHER PUBLICATIONS

Corresponding International Patent Application No. PCT/US2023/
036125, Written Opinion of the Searching Authority, date mailed
Feb. 1, 2024.
Corresponding International Patent Application No. PCT/US2023/
036125, International Preliminary Report on Patentability, dated
May 8, 2025.
Burdick, J.A., et al., "Controlled Degradation and Mechanical
Behavior of Photopolymerized Hyaluronic Acid Networks",
Biomacromolecules, Nov. 24, 2024, vol. 6, Issue 1, pp. 386-391.
Tan, Donald T.H., et al., "Randomized clinical trial of surodex
steroid drug delivery system for cataract surgery: Anterior versus
posterior placement of two surodex in the eye", Ophthalmology,
vol. 108, Issue 12, Dec. 2001, pp. 2172-2181.

* cited by examiner

A

B

A 16                    16

B

16

16

20

26

24

24

DRUG DELIVERING STRETCH RING

CROSS-REFERENCE TO RELATED APPLICATIONS

This application claims priority to U.S. Provisional Patent Application Ser. No. 63/419,738, filed Oct. 27, 2022, which is incorporated herein by reference.

BACKGROUND

Cataract surgery is the most frequently performed ocular procedure worldwide. Eye drops for the administration of antibiotics and steroids are usually prescribed following cataract surgery to prevent infection and reduce pain and inflammation and facilitate healing. However, topical administration of eye drops can be difficult for the patient. There may be low intraocular bioavailability due to poor corneal penetration. Topical medications usually have a short duration of action, requiring frequent application of the drops, which may be difficult for the patient and may require repeated trips to the ophthalmologist for administration. In some cases there are also adverse reactions to eye drugs following cataract surgery, such as eye irritation, eye redness, and headache.

Different drug delivery systems have been developed to provide alternatives to the use of eye drops to control infection and inflammation after cataract surgery. For example, a dexamethasone anterior segment drug delivery system (Surodex™) has been shown to be effective to treat inflammation after cataract surgery. However, this device had several disadvantages such as expense and difficulty in removal, and adverse effects such as implant migration and peripheral anterior synechiae have been reported. Tan et al., Ophthalmology, 108:2172-2181 (2001). Likewise, while IOLs have been developed as drug delivery devices (Liu et al., Curr Opin Ophthalmol, 24, 53-59 (2013), these are also subject to a variety of limitations. Accordingly, there remains a need for a safe and easy method to deliver drugs to the eye, in particular after implantation of an intraocular lens during cataract surgery.

SUMMARY OF THE INVENTION

The present invention provides a non-permanent device that can dissolve and provide temporary support to either the IOL or to the lens capsule. In some embodiments, the device can also contain a sustained release agent.

In one aspect, the present invention provides a polymer ring configured to fit around an intraocular lens, the polymer ring comprising a hyaluronic acid derivative and a drug. In some embodiments, the hyaluronic acid derivative is methacrylated hyaluronic acid. In further embodiments, the drug is an ophthalmological drug, such as an antibiotic and/or a steroid.

In some embodiments, the polymer ring is biodegradable. In additional embodiments, the drug is formulated for sustained release from the polymer ring. In further embodiments, the intraocular lens is an accommodating intraocular lens. In yet further embodiments, the intraocular lens includes a plurality of haptics, and the polymer ring includes a plurality of tabs that fit between the haptics of the intraocular lens.

Another aspect of the invention provides a method of delivering a drug to an eye of a subject. The method includes the steps of inserting an intraocular lens into the eye of the subject and positioning polymer ring onto the intraocular lens, wherein the polymer ring comprises a hyaluronic acid derivative and a drug. In some embodiments, intraocular lens is inserted into the eye of the subject after removal of the natural lens of the subject in cataract surgery.

In some embodiments, the hyaluronic acid derivative is methacrylated hyaluronic acid. In further embodiments, the intraocular lens is an accommodating intraocular lens. In additional embodiments, the polymer ring is biodegradable. In yet further embodiments, the drug is an ophthalmological drug, such as an antibiotic and/or a steroid.

Another aspect of the invention provides an IOL comprising an IOL body comprising at least one haptic extending directly or indirectly from the IOL body; and a polymer ring comprising a hyaluronic acid derivative and a drug positioned on the at least one haptic of the IOL.

DETAILED DESCRIPTION OF THE INVENTION

Figure 1A:
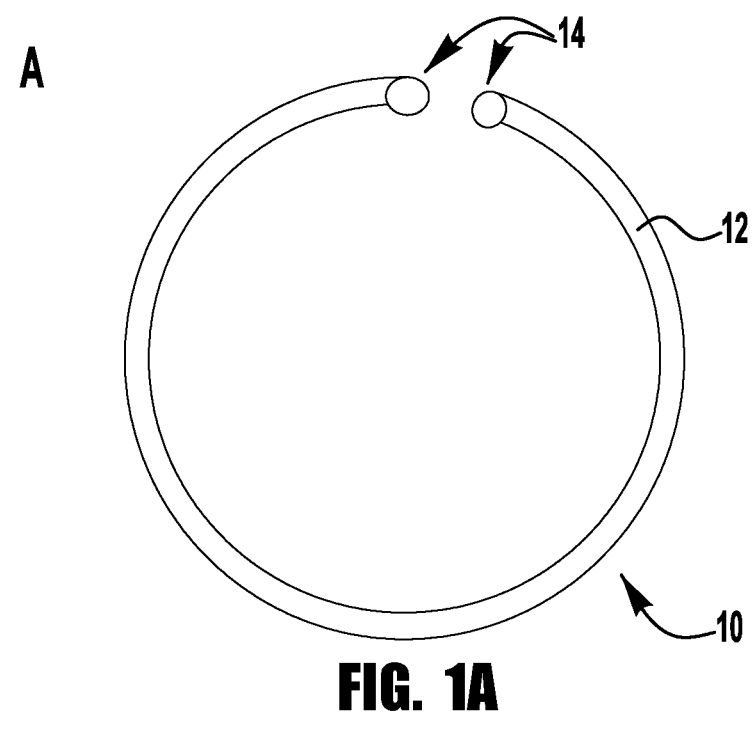
FIGS. 1A and 1B provide a representation of A) a drug-delivering stretch ring and b) the drug-delivering stretch ring positioned over or adjacent to the haptics of an intraocular lens.

The present invention provides a polymer ring configured to fit around or adjacent to at least a portion of an intraocular lens or within the lens capsule. The polymer ring includes a hyaluronic acid derivative and a drug. A method of delivering a drug to an eye of a subject is also provided. The method includes inserting an intraocular lens into the eye of the subject, and positioning polymer ring onto at least a portion of the intraocular lens, wherein the polymer ring comprises a hyaluronic acid derivative and a drug.

The terminology as set forth herein is for description of the embodiments only and should not be construed as limiting of the invention as a whole. Unless otherwise specified, "a," "an," "the," and "at least one" are used interchangeably. Furthermore, as used in the description of the invention and the appended claims, the singular forms "a", "an", and "the" are inclusive of their plural forms, unless contraindicated by the context surrounding such.

Also herein, the recitations of numerical ranges by endpoints include all numbers subsumed within that range (e.g., 1 to 5 includes 1, 1.5, 2, 2.75, 3, 3.80, 4, 5, etc.).

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

The terms "comprises," "comprising," "includes," "including," "having" and their conjugates mean "including but not limited to". This term encompasses the terms "consisting of" and "consisting essentially of".

A "subject," as used herein, can be any animal, and may also be referred to as the patient. Preferably the subject is a vertebrate animal, and more preferably the subject is a mammal, such as a research animal (e.g., a mouse or rat) or a domesticated farm animal (e.g., cow, horse, pig) or pet (e.g., dog, cat). In some embodiments, the subject is a human.

The terms "therapeutically effective" and "pharmacologically effective" are intended to qualify the amount of each agent which will achieve the goal of decreasing disease severity while avoiding adverse side effects such as those typically associated with alternative therapies. The therapeutically effective amount may be administered in one or more doses.

"Biocompatible" as used herein, refers to any material that does not cause injury or death to a subject or induce an adverse reaction in a subject when placed in contact with the subject's tissues. Adverse reactions include for example inflammation, infection, fibrotic tissue formation, cell death, or thrombosis. The terms "biocompatible" and "biocompatibility" when used herein are art-recognized and mean that the material is neither itself toxic to a subject, nor degrades (if it degrades) at a rate that produces byproducts at toxic concentrations, does not cause prolonged inflammation or irritation, or does not induce more than a basal immune reaction in the host.

The term "biodegradable" as used herein refers to a biocompatible polymer that can be broken down by either chemical or physical process, upon interaction with the physiological environment subsequent to use, and erodes or dissolves within a period of time, typically within days, weeks or months. A biodegradable material serves a temporary function in the body, such as imaging a tissue region, and is then degraded or broken into components that are metabolizable or excretable.

Drug-Delivering Stretch Ring

In one aspect, the present invention provides a polymer ring (i.e., a drug-delivering stretch ring) comprising a hyaluronic acid derivative and a drug. The polymer ring can be configured to rest on a portion of the eye, or it may be configured to fit around at least a portion of an intraocular lens. The polymer ring may be any suitable form, such as a ring, a partial ring or ring segment, multiple ring segments, or a polygon. In some embodiments, the polymer ring is configured to fit around the circumference of the intraocular lens, while in other embodiments the polymer ring is configured to rest on the haptics of the intraocular lens.

The dimensions of the drug-delivering stretch ring should be selected to facilitate placement on the eye or an intraocular lens. Preferably the drug-delivering stretch ring has a diameter from about 5 mm to about 15 mm, or in some embodiments from about 10 to about 15 mm. A diameter of about 11 to about 13.5 mm is preferred for placement on the periphery of the capsular bag adjacent to the IOL, while a diameter of about 9.5 mm to about 10.5 mm is preferred to placement on the haptics of an accommodating IOL. The width or thickness of the ring is typically 2 mm or less (e.g., from about 0.2 mm to about 1.5 mm).

The drug-delivering stretch ring comprises a hyaluronic acid derivative. Hyaluronic acid derivatives are hyaluronic acid polymers that have been modified to include an additional chemical group. Examples of hyaluronic acid derivatives include hyaluronic acid alkyl derivatives. An example of a specific hyaluronic acid derivative is methacrylated hyaluronic acid. In further embodiments, the polymer ring is biodegradable. The polymer ring can comprise at least 50%, at least 60%, at least 70%, at least 80%, at least 90%, or 100% hyaluronic acid derivative, with the remain comprising other biocompatible polymers known to those skilled in the art.

Hyaluronan ("hyaluronic acid," "HA", or [$\alpha$-1,4-D-glucuronic acid-$\beta$-1,3-N-acetyl-D-glucosamine]n) is a naturally occurring high molecular weight hydrophilic glycosaminoglycan. It is a linear polymer with high molecular weight linear polysaccharide containing alternating N-acetyl-D-glucosamine and D-glucuronic acid residues. Derivatives of hyaluronic acid include branched polysaccharides containing alternating N-acetyl-D-glucosamine and D-glucuronic acid residues, and also include the incorporation of further chemical moieties, such as fluorescent labels, glycidyl groups, or protecting groups. Suitable derivatives of hyaluronic acid include, but are not limited to, cetyltrimethylammonium silylhyaluronate (silyl HA-CTA), cetyltrimethylammonium hyaluronate (HA-CTA), hyaluronan salt complex HA2-QN+, trimethylsilane-protected hyaluronan salt complex, fluorescein-tagged hyaluronic acid, glycidyl methacrylated hyaluronic acid, and fluorescein-tagged glycidyl methacrylated hyaluronic acid. Hyaluronic acid polymer derivatives have shown to have good properties for carrying and releasing drugs. Buckley et al., Polymers (Basel), 14(17):3442 (2022). Methacrylated HA (MeHA) hydrogels have shown increased rigidity and are more resistant to degradation, compared to non-derivatized HA hydrogels, while maintaining good biocompatibility. Burdick et al., Biomacromolecules 6 (1):386-391 (2005). Accordingly, in some embodiments the hyaluronic acid derivative is methacrylated hyaluronic acid.

The polymer ring contains at least one drug. In some embodiments, the drug is selected from the group comprising anti-fibrotic agent, anti-inflammatory agent, immunosuppressant agent, anti-neoplastic agent, migration inhibitors, anti-proliferative agent, intraocular pressure lowering agents, rapamycin, triamcinolone acetonide, everolimus, tacrolimus, paclitaxel, actinomycin, azathioprine, dexamethasone, cyclosporine, bevacizumab, an anti-VEGF agent, an anti-IL-1 agent, canakinumab, an anti-IL-2 agent, viral vectors, beta blockers, alpha agonists, muscarinic agents, steroids, antibiotics, non-steroidal anti-inflammatory agents, prostaglandin analogues, ROCK inhibitors, nitric oxide, endothelia, matrix metalloproteinase inhibitors, CNPA, corticosteroids, cenegermin, cyclosporine, cysteamine hydrochloride, mitomycin, sodium chloride hypertonic, netarsudil, and riboflavin 5'phosphate and/or antibody-based immunosuppressants.

In some embodiments, the drug is an ophthalmological drug. An ophthalmological drug is one that is routinely prescribed for use in or on the eye, such as after cataract surgery. Examples of categories of ophthalmological drugs include antibiotics, intraocular pressure lowering agents, and anti-inflammatory agents such as steroids. Examples of specific ophthalmological drugs include sodium hyaluronate, triamcinolone acetonide, dexamethasone, cyclosporine, bevacizumab, an anti-VEGF agent, an anti-IL-1 agent, an anti-IL-2 agent, viral vectors, beta blockers, alpha agonists, muscarinic agents, steroids, antibiotics, nonsteroidal anti-inflammatory agents, prostaglandin analogues, ROCK inhibitors, nitric oxide, matrix metalloproteinase inhibitors, CNPA, corticosteroids. In some embodiments, the drug is an antibiotic and/or a steroid.

In some embodiments, the drug-releasing stretch ring provides sustained release of the drug into the eye. A variety of release kinetics are contemplated for the timed release of drug(s) from the polymer ring, including bi- or multi-phase release, such as an initial fast release followed by a slower subsequent release phase or delay the initial release for a certain period of time and then rapid or sustained release. For example, the release may include a burst release of drug from the polymer ring rapidly within seconds or minutes followed by further sustained release over a period of at least 2, 4, 6, 8 or more hours, days, weeks and/or months. Such longer-term release can be referred to as sustained or prolonged release. Such release kinetics may be advantageous in certain circumstances, e.g., where sustained action is desired, in comparison with, e.g., a burst of drug from an eyedrop.

The hyaluronic acid derivative can naturally provide sustained release of the drug from the polymer ring. However, in some embodiments the polymer ring can be modified by including a hollow drug-retaining section, pores, or micropores in order to further support drug retention and release. In some embodiments, the drug itself can be modified (e.g., formulated) for sustained release, by providing a carrier for the drug or by providing the drug in a prodrug form.

FIG. 1A provides an image of a drug-delivering stretch ring. The drug-delivering stretch ring 10 includes an open ring 12 made of a biodegradable polymer, and an eyelet 14 at each end of the open ring. The drug-delivering stretch ring may be circular in its resting state, or it may simply be capable of forming a circle when placed upon the haptics of an intraocular lens, or when placed within the lens capsule of the eye.

Figure 2A:
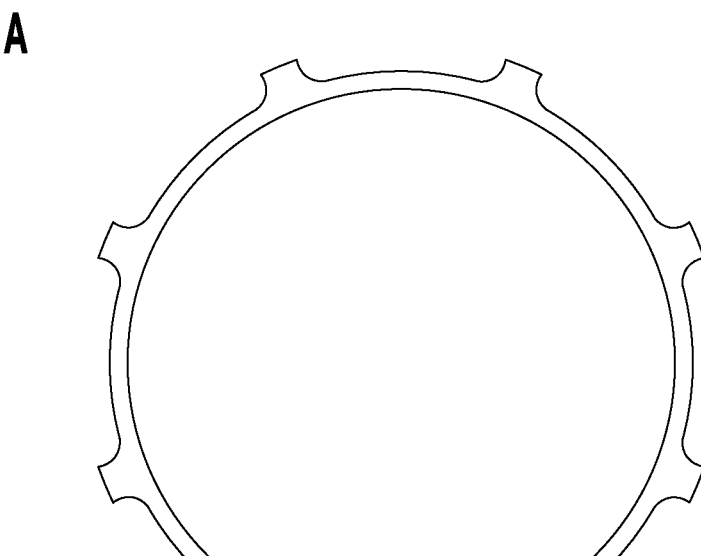
FIGS. 2A and 2B provide a representation of A) a drug-delivering stretch ring including positioning tabs and B) the drug-delivering stretch ring including positioning tabs positioned on a multi-arm intraocular lens.

A further embodiment of the drug-delivering stretch ring is shown in FIG. 2A. In this embodiment, the drug-delivering stretch ring 10 includes a plurality of positioning tabs 16 configured to fit between the haptics of the intraocular lens. In many embodiments, the positioning tabs 16 are positioned at regular intervals around the circumference of the drug-delivering stretch ring. The drug-delivering stretch ring can include a number of positioning tabs equal to the number of haptics present on the intraocular lens. For example, when configured to fit between the haptics of an intraocular lens having eight haptics, the drug-delivering stretch ring can include eight positioning tabs.

Method of Implanting an Intraocular Lens

Another aspect of the invention provides a method of delivering a drug to an eye of a subject. The method includes inserting an intraocular lens (IOL) into the eye of the subject, and positioning polymer ring onto at least a portion of the IOL, wherein the polymer ring comprises a hyaluronic acid derivative and a drug. Once placed in the eye, the polymer ring will release drug into the eye and its surrounding fluid. Alternately, in some embodiments, the IOL can be positioned on at least a portion of the IOL before the IOL is inserted into the eye of a subject.

The polymer ring, the drug, and the intraocular lens can have any of the features and characteristics described herein. In some embodiments, the hyaluronic acid derivative is methacrylated hyaluronic acid, while in further embodiments the polymer ring is biodegradable. In additional embodiments, wherein the intraocular lens is an accommodating intraocular lens. In yet further embodiments, the drug is an ophthalmological drug, such as an antibiotic and/or a steroid. In some embodiments, a plurality of drug-delivering stretch rings can be positioned in the eye of a subject, where the plurality of drug-delivering stretch rings can deliver different drugs and/or provide better drug distribution within the eye.

In some embodiments, the intraocular lens is inserted into the eye of the subject after removal of the natural lens of the subject in cataract surgery. A cataract is a clouding or development of an opaque area in the lens. Most cataracts form as part of the aging process, but some are associated with congenital or systemic pathological conditions and others are related to ocular trauma. Cataracts are formed by the clumping of the proteins in the lens and the opacification that ensues, which hinders light transmission and normal vision. In cataract surgery, a portion of the lens anterior capsule is removed, and an artificial intraocular lens is inserted into the eye, typically within the remaining lens capsule. Following cataract surgery, it is common to administer anti-inflammatory and/or antibiotic drugs to prevent inflammation and/or infection following surgery.

Figures 3A, 3B:
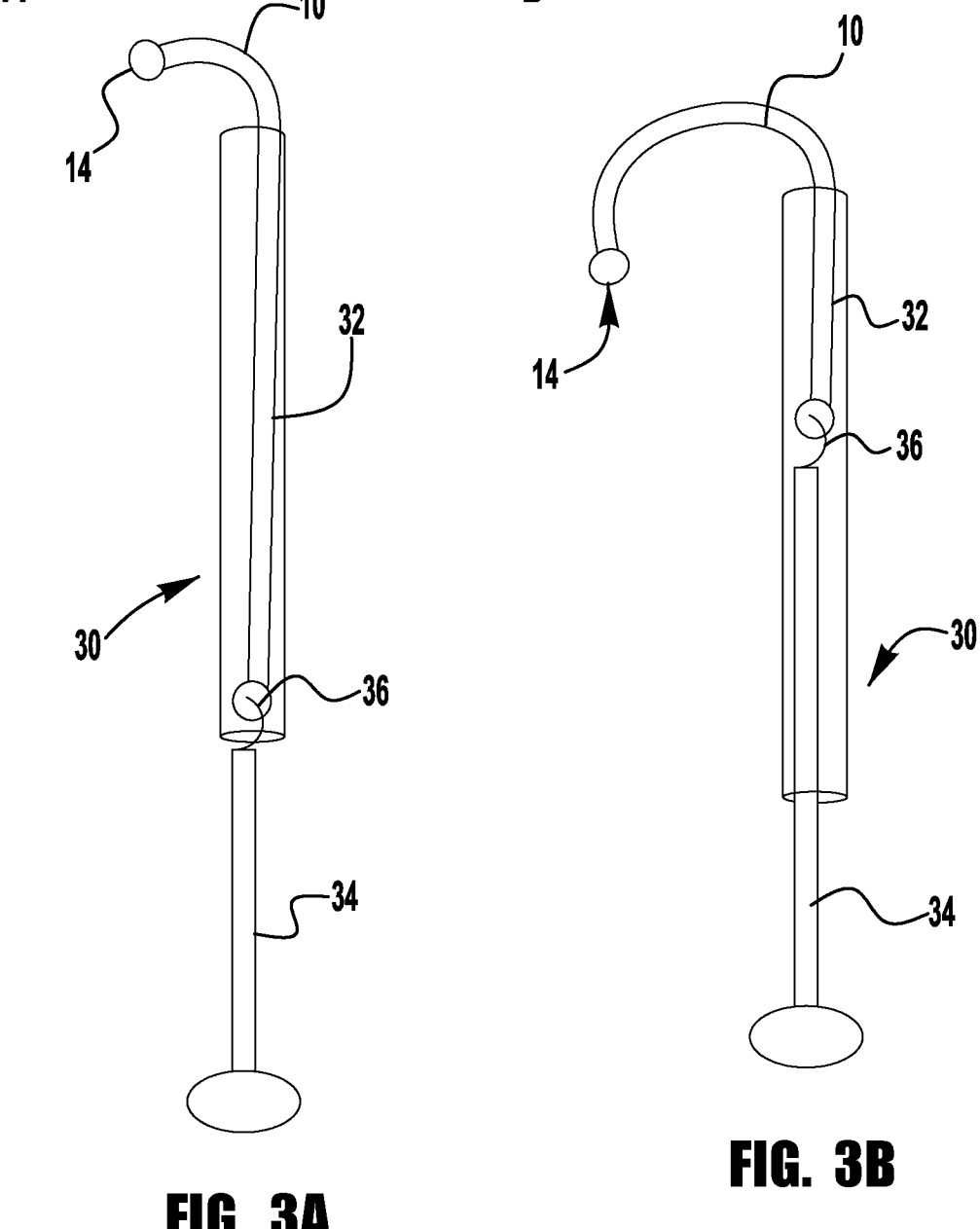
FIGS. 3A and 3B provide a representation of an implantation device for a drug-delivering stretch ring, with A) showing the drug-delivering stretch ring within the implantation device before use, and B) showing the extruded drug-delivering stretch ring after pressure had been applied to a push rod of the implantation device.

The drug-delivering stretch ring can be positioned on the intraocular lens, or within the lens capsule, using an implantation device. An implantation device 30 suitable for use with a drug-delivering stretch ring is shown in FIG. 3. The implantation device 30 include a sleeve 32 in which the drug-delivering stretch ring 10 is held, and a push rod 34 that fits within the sleeve 32. FIG. 3A shows the drug-delivering stretch ring within the implantation device before use, while FIG. 3B shows the extruded drug-delivering stretch ring 10 after pressure had been applied to a push rod 34 of the implantation device 30. In some embodiments, the pressure rod 34 includes a hook 36 that can fit into an eyelet 14 of the drug-delivering stretch ring 10 to facilitate handling of the drug-delivering stretch ring 10.

Intraocular Lens Including a Drug Delivering Stretch Ring

A further aspect of the invention relates to an arrangement of the drug-delivering stretch ring with ophthalmic devices including IOLs and more particularly to accommodating intraocular lenses (accommodating IOLs). In some embodiments, the IOL comprises a shape-changing optic. The IOL can be configured to assume an accommodated state, a dis-accommodated state, and states therebetween.

In some embodiments, the present invention provides an IOL comprising an IOL body and at least one haptic extending directly or indirectly from the IOL body, and a polymer ring comprising a hyaluronic acid derivative and a drug positioned on or adjacent to the at least one haptic of the IOL. In some embodiments, the IOL is an accommodating IOL.

In some embodiments, the intraocular lens includes a plurality of haptics, and the polymer ring includes a plurality of tabs that fit between the haptics of the intraocular lens. IOLs often include plastic side struts, called haptics, to hold the lens in place in the capsular bag inside the eye. In a further embodiment, the polymer ring includes a plurality of positioning tabs configured to fit between the plurality of haptics.

In some embodiments, the drug-delivering ring can be incorporated into the IOL itself. For example, the drug-delivering ring can form a stabilizing ring to keep the haptics from holding inwards with lens capsule fibrosis. See for example the stabilizing ring described in WO 2022/016130, the disclosure of which is incorporated herein by reference.

Figure 1B:
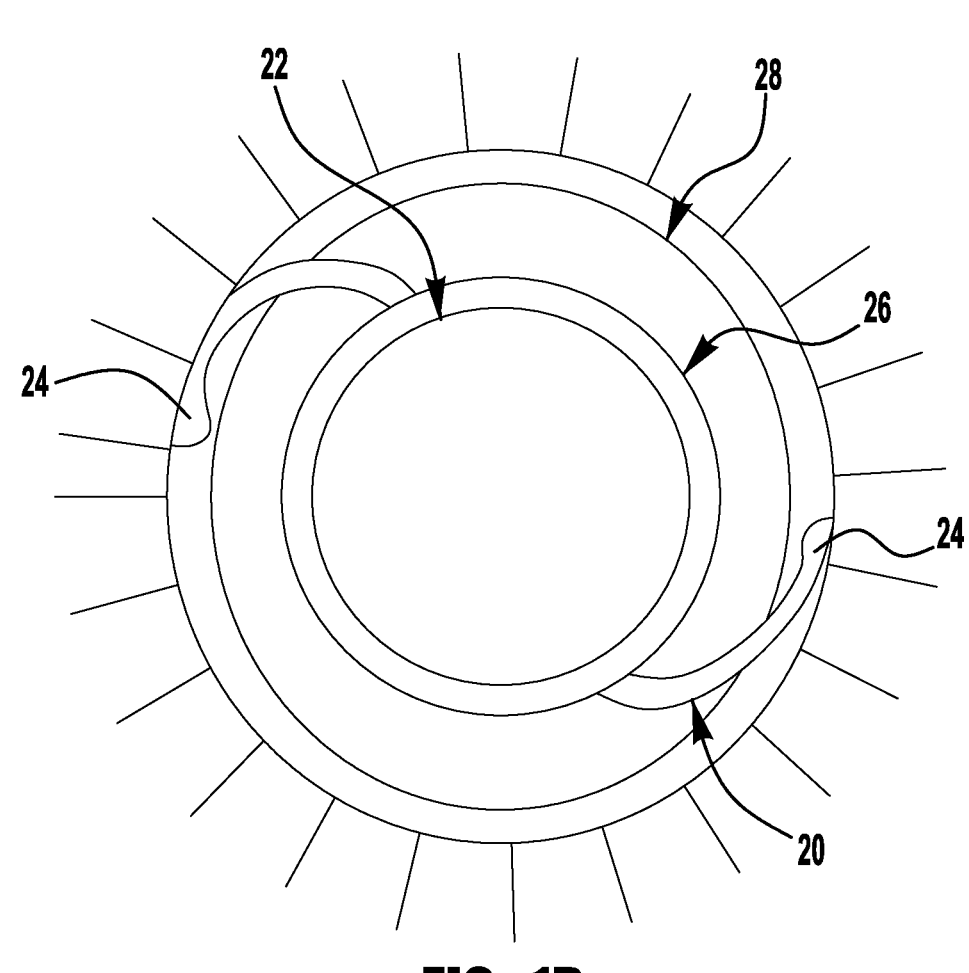

FIG. 1B shows an intraocular lens arrangement. The intraocular lens 20 has been positioned over the anterior opening 22 in the lens capsular bag. The intraocular lens 20 includes a pair of haptics 24 that extend from the body 26 of the intraocular lens 20 to the peripheral lens capsular bag 28. The arrangement also includes a drug-delivering stretch ring 10 positioned over or adjacent to the haptics 24 and along the edge of the peripheral capsular bag 28.

Figure 2B:
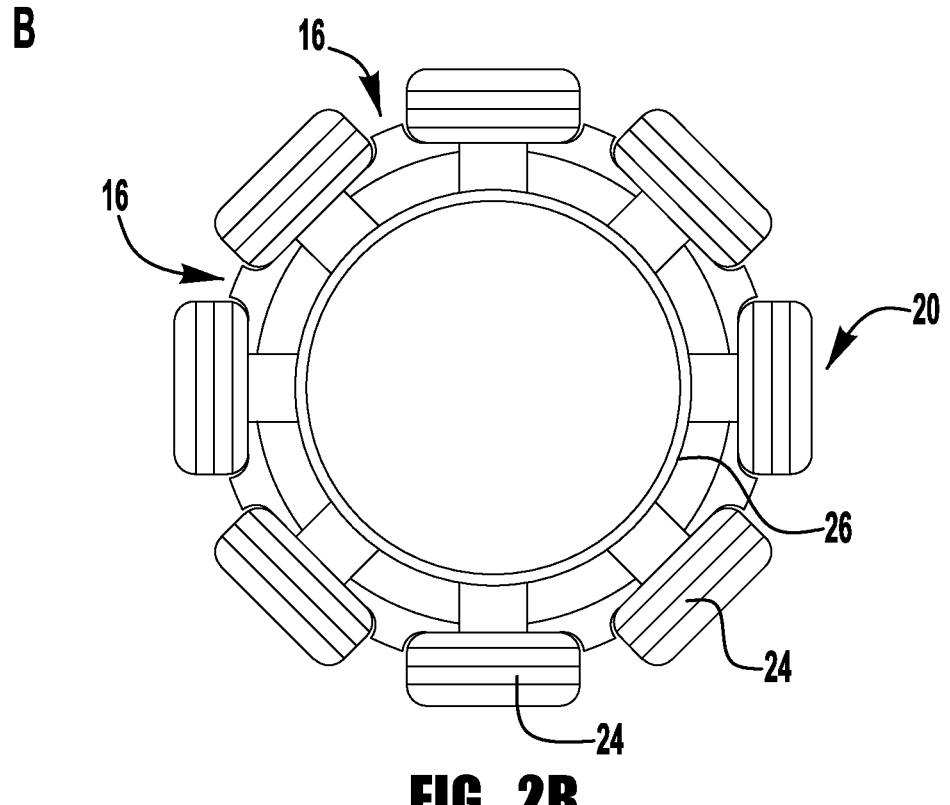

FIG. 2B shows an intraocular lens arrangement including a drug-delivering stretch ring comprising a plurality of positioning tabs 16. In this embodiment, the intraocular lens 20 includes a plurality of haptics 24 positioned around the body 26 of the intraocular lens 20. The positioning tabs 16 are positioned between the haptics 24 of the intraocular lens. In some embodiments, the drug-delivering stretch ring 10 includes a plurality of positioning tabs 16 configured to fit between the haptics 24 of the intraocular lens 20.

In some embodiments, the hyaluronic acid derivative comprises methacrylated hyaluronic acid. In further embodiments, the drug is an ophthalmological drug. The drug-delivering stretch ring included in the assembly can include any of the features described herein.

In some embodiments, the present invention relates to an arrangement of the drug-delivering stretch ring with ophthalmic devices including IOLs and more particularly to accommodating intraocular lenses (accommodating IOLs). In an aspect, an IOL can comprise a shape-changing optic. The IOL can be configured to assume an accommodated state, a dis-accommodated state, and states therebetween. The IOL can comprise an elastic anterior face located anterior to the equator, having an anterior surface and a posterior surface, and having a periphery. The IOL can also include a posterior face having an anterior surface, a posterior surface, and a periphery. The IOL can further include an elastic side wall extending across the equator and extending from the anterior face to the posterior face. The IOL additionally can include a chamber containing material that is located between the anterior face and the posterior face. The IOL can also include at least one haptic having a medial portion and a lateral portion. The medial portion can extend (directly or indirectly) from the periphery of the anterior face, the periphery of the posterior face, or both. In certain aspects, the at least one haptic comprises a plurality of haptics, each having a medial portion and a lateral portion, the medial portion extending from and connected to the periphery of the anterior face such that the plurality of haptics changes the shape of the anterior face via tensile or compressive forces. The anterior face can be more resistant to deformational change than the material contained within the chamber. See U.S. Pat. No. 11,357,618, the disclosure of which is incorporated herein by reference.

In another aspect, an IOL has an optical axis extending in an anterior-posterior direction and an equator extending in a plane substantially perpendicular to the optical axis. The IOL can comprise an elastic anterior face located anterior to the equator, and a posterior face located posterior to the equator. The anterior face, the posterior face, or both can comprise a poly(dimethylsiloxane) elastomer having a durometer between about 30 Shore A to about 50 Shore A. A chamber can be located between the anterior face and the posterior face and can comprise a silicone oil comprising polysiloxanes comprising diphenyl siloxane and dimethyl siloxane units. The silicone oil has a maximum viscosity of about 700 mm²/s at 25° C. and has a mean molecular weight of less than about 3000 Daltons.

In another aspect, the IOL has an optical axis extending in an anterior-posterior direction and an equator extending in a plane substantially perpendicular to the optical axis. The IOL can comprise an elastic anterior face located anterior to the equator and a posterior face located posterior to the equator. The anterior face, the posterior face, or both can comprise a polysiloxane that is at least 99% poly(dimethylsiloxane) elastomer. The IOL can further include a chamber located between the anterior face and the posterior face and can comprise a silicone oil comprising polysiloxanes comprising diphenyl siloxane and dimethyl siloxane units.

The complete disclosure of all patents, patent applications, and publications, and electronically available materials cited herein are incorporated by reference. Any disagreement between material incorporated by reference and the specification is resolved in favor of the specification. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A polymer ring configured to fit around or adjacent to at least a portion of an intraocular lens (IOL), the polymer ring comprising methacrylated hyaluronic acid and a drug.

2. The polymeric ring of claim 1, wherein the drug is an ophthalmological drug.

3. The polymeric ring of claim 1, wherein the drug is an antibiotic and/or a steroid.

4. The polymer ring of claim 1, wherein the polymer ring is biodegradable.

5. The polymer ring of claim 1, wherein the drug is formulated for sustained release from the polymer ring.

6. The polymer ring of claim 1, wherein the IOL is an accommodating IOL.

7. The polymer ring of claim 1, wherein the IOL includes a plurality of haptics extending directly or indirectly from a body of the IOL.

8. The polymer ring of claim 7, wherein the intraocular lens includes a plurality of tabs that fit between the plurality of haptics.

* * * * *